US005572745A

United States Patent [19]
Mainus

[11] Patent Number: 5,572,745
[45] Date of Patent: Nov. 12, 1996

[54] WEARING APPAREL INCLUDING A COOLING MATERIAL

[75] Inventor: Edward Mainus, Wilmington, Calif.

[73] Assignee: Cool Wear Works, Inc., Long Beach, Calif.

[21] Appl. No.: 311,503

[22] Filed: Sep. 23, 1994

[51] Int. Cl.$^6$ .................................................. A42B 1/18
[52] U.S. Cl. .................. 2/171.2; 2/195.1; 2/DIG. 11; 2/7
[58] Field of Search .................. 2/171.2, 7, 181, 2/195.1, 209.13, 2, 7, 170, 181.2, DIG. 11; 607/109, 110, 108, 111, 112, 114

[56] References Cited

U.S. PATENT DOCUMENTS

| | | | |
|---|---|---|---|
| 1,377,107 | 5/1921 | Westrope | 2/181 |
| 1,689,539 | 10/1928 | Wagner | 2/171.2 |
| 2,562,121 | 7/1951 | Poux | 607/108 |
| 2,875,447 | 3/1959 | Goldmerstein | 2/171.2 |
| 3,092,112 | 6/1963 | Zelony | 2/171.2 |
| 3,349,825 | 10/1967 | Andreadis | 2/171.2 |
| 4,484,363 | 11/1984 | Varanese | 2/181 |
| 4,551,858 | 11/1985 | Pasternack | 2/7 |
| 4,742,581 | 5/1988 | Rosenthal | 2/181 |
| 4,805,619 | 2/1989 | Swearingen | 128/380 |
| 4,815,144 | 3/1989 | Martin | 2/171.2 |
| 5,129,391 | 7/1992 | Brodsky et al. | 128/402 |
| 5,146,630 | 9/1992 | Richard | 2/171.2 |
| 5,150,707 | 9/1992 | Anderson | 128/402 |
| 5,305,470 | 4/1994 | McKay | 2/170 |
| 5,327,585 | 7/1994 | Karlan . | |

Primary Examiner—Amy B. Vanatta
Attorney, Agent, or Firm—Richard L. Myers

[57] ABSTRACT

A visor adapted to be worn on the head of a user includes a browband having a top surface and a bottom surface extending between a first end and a second end. An attachment strap extends between the first and second end to form with the browband a headband variable in length to facilitate snug engagement on the head of the user. A sunshade extends outwardly from the bottom surface of the browband in a fixed relationship with the headband. A first tube is included in the browband and has a first axis extending between the first end and the second end of the browband. Similarly, a second tube is included in the browband and has a second axis. The first tube is disposed tangential to the second tube with the first axis generally parallel to the second axis. A water absorbent cooling material is disposed in at least one of the first and second tube to facilitate evaporation while cooling the head of the user.

15 Claims, 5 Drawing Sheets

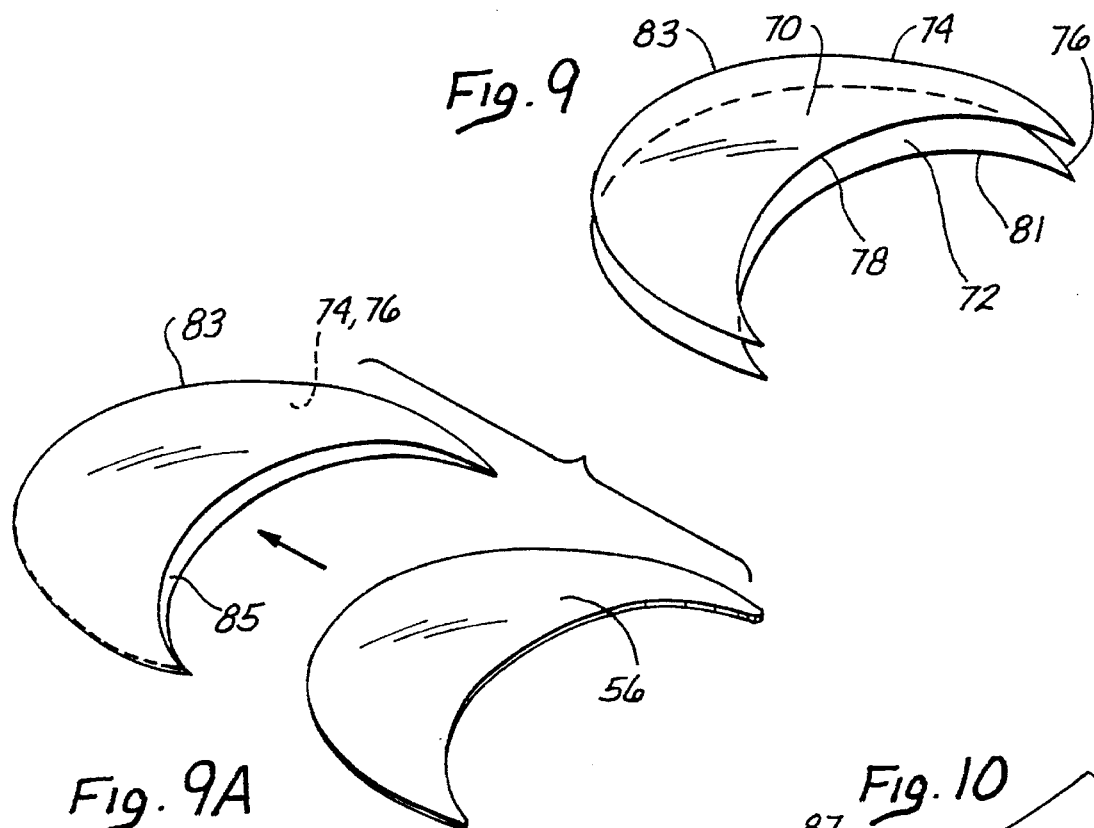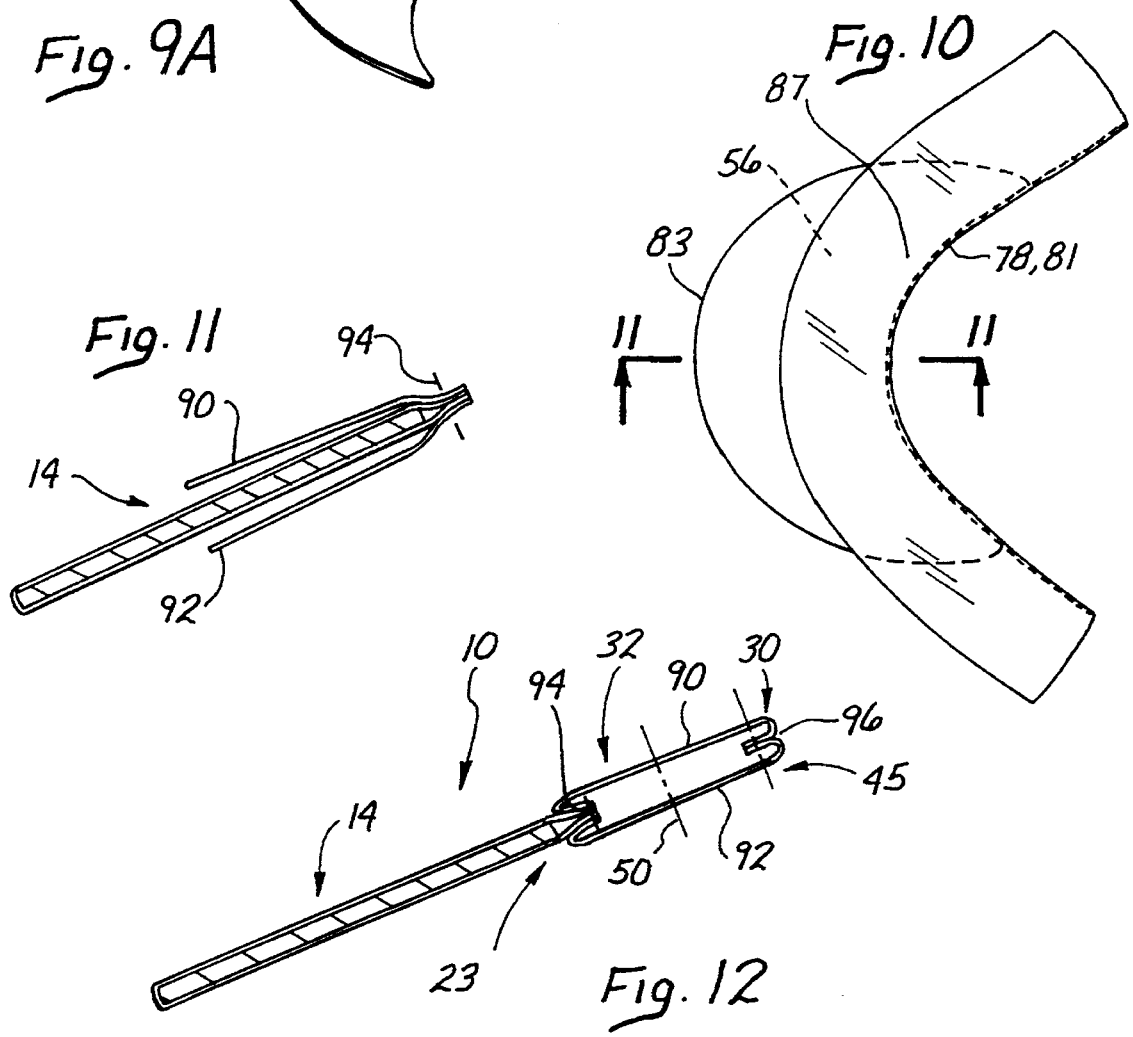

WEARING APPAREL INCLUDING A COOLING MATERIAL

BACKGROUND OF THE INVENTION

1. Field of the Invention

This invention relates generally to apparel adapted to be worn by a person and to carry water absorbent crystals for cooling the person upon evaporation of water from the crystals.

2. Discussion of the Prior Art

It is well known that water evaporating from the skin has a cooling influence on body temperature. In a more theoretical sense, water on the skin at 100% humidity is attracted to the vapor state because the surrounding air has a humidity which is less than 100%. As the change from liquid to vapor occurs, heat is drawn from the skin at a temperature which is less than body temperature. Accordingly, the evaporating water feels cool. It is also known that if this cooling occurs at certain regions of the body, the overall cooling effect is greatly enhanced. For example, since there is a high concentration of blood vessels and blood flow in proximity to the wrist, evaporation in this region tends to have a cooling effect throughout the body.

Visors of the past have incorporated water absorbent crystals in a single tubular cavity which extends around the forehead of the individual wearing the visor. In order to provide a substantial area of contact, a large volume of the crystals has been required thereby rendering the visor bulky, heavy and costly to manufacture. The tubular enclosure which contained the crystals in visors of the prior art formed a headband which extended around substantially the entire head of the user. This further contributed to the weight, volume and high cost associated with these visors.

In the past absorbent crystals were provided in an impure form that was toxic to some people. Rashes were the most common result of this toxicity.

SUMMARY OF THE INVENTION

These deficiencies of the prior art have been overcome with the present invention which includes crystals that exhibit both hydroscopic and hydrophilic properties. Importantly, these crystals are chemically neutral and 100% non-toxic. In one form of the invention, a visor encloses the crystals in a browband formed of more than one tube, which extend around less than the entire circumference of the head. In one embodiment, these crystal-containing tubes are limited to the forehead of the person, where the browband is in direct contact with skin. By limiting the cooling action to the forehead, more than half of the bulk and volume associated with the visor can be eliminated. It has also been found that a particular configuration for the browband can even further reduce the volume of the crystals.

In general, it is desirable to maximize the area of contact while minimizing the volume of the crystals. Maximizing the ratio of area to volume reduces the weight, cost and bulk of the crystals without sacrificing the cooling effect which is proportional to the area. Where the tubes have a circular cross-sectional configuration the ratio of area to volume is given generally by the formula $$4X/\pi h$$

where "X" is the number of tubes and "h" is the height of the browband. It follows that for a constant area of contact the ratio of area to volume is directly proportional to the number of tubes.

While this ratio is of particular interest, it must also be appreciated that the greater the volume of crystals, the more water is absorbs, and the longer is the period over which evaporation takes place. For this reason, maximum benefit is achieved where the area to volume ratio is considered along with the volume required for a prolonged period of cooling. In a preferred embodiment, two tubes are included in the browband in order to further reduce the weight and bulk associated with the prior art.

In one aspect of the invention, a visor is adapted to be worn on the head of a user and comprises a browband having an top surface, and a bottom surface each extending between a first end and a second end. Attachment means extends between the first and second ends of the browband for forming with the browband a headband. The attachment means has a variable length to facilitate snug engagement of the headband with the head of the user. The visor includes a sun shade extending outwardly from the bottom surface of the browband in a fixed relationship with the browband. A first tube of the browband has a first axis and defines the top surface between the first end and the second end of the browband. At least one second tube of the browband has a second axis and defines the bottom surface between the first end and the second end of the browband. The first tube is disposed tangentially of the second tube with the first axis generally parallel with the second axis. A cooling material is disposed in at least one of the first and second tube which absorbs water and has a cooling effect when the water evaporates from the cooling material.

These and other features and advantages of the invention will be more apparent with a description of preferred embodiments and reference to the associated drawings.

DESCRIPTION OF THE DRAWINGS

FIGS. 9–12 illustrate a preferred method for making a visor of the present invention;

FIG. 9 is a top view of fabric pieces being sewn to form an eyeshade subassembly;

FIG. 9a is a top view of the fabric pieces inverted to form a pocket for an insert in the eyeshield subassembly;

FIG. 10 is a top plan view of the eyeshade subassembly in completed form;

FIG. 11 is a cross section view taken along lines 11—11 of FIG. 10 and illustrating formation of a browband with the eyeshade subassembly;

FIG. 12 is a cross section view similar to FIG. 11 and illustrating a further step for forming tubes of the browband;

FIG. 17 is a perspective view of a headband adapted to be worn on the head of a user;

FIG. 18 is a perspective view of a neckband adapted to be worn around the neck of a user; and FIG. 19 is a perspective view of a wristband of the present invention adapted to be worn on the wrist of a user.

DESCRIPTION OF PREFERRED EMBODIMENTS AND BEST MODE OF THE INVENTION

Figure 1:
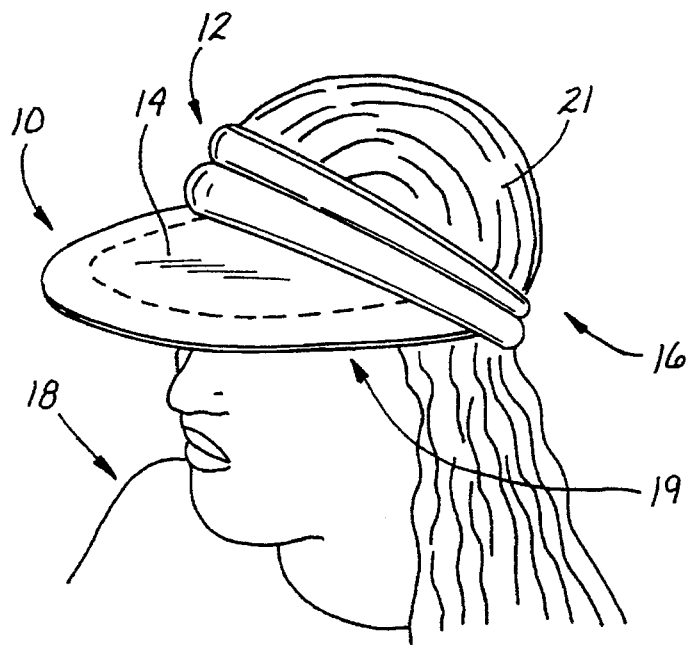
FIG. 1 is a perspective view of a visor embodying the concept of the present invention and adapted for disposition upon the head of the user.
Figure 2:
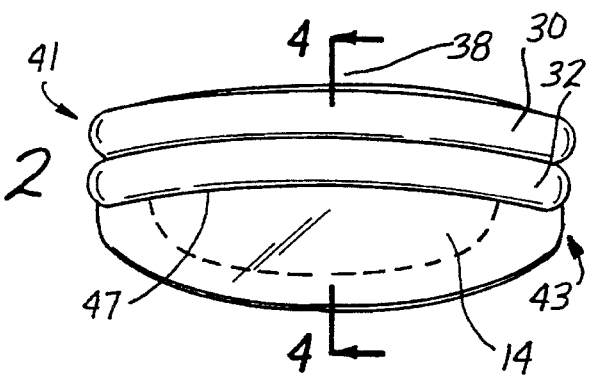
FIG. 2 is a front elevation view of the visor illustrated in FIG. 1.

A visor is illustrated in FIG. 1 and designated generally by the reference numeral 10. The visor 10 includes a headband 12 and an eyeshade 14. It is adapted for use on a head 16 of a user 18, where the headband 12 extends around the forehead 19 and hair 21, and the eyeshade 14 extends outwardly from the forehead 19 over the eyes of the user 18.

Figure 3:
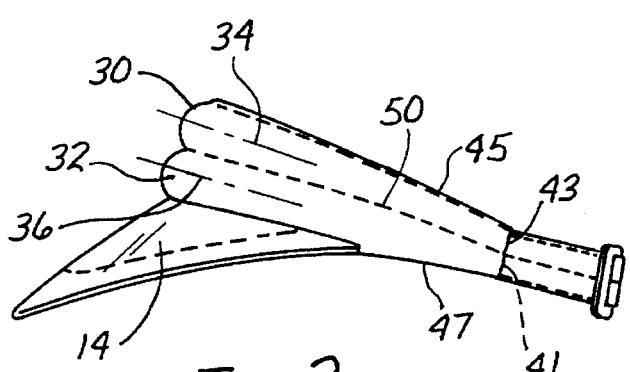
FIG. 3 is a side elevation view of the visor illustrated in FIG. 1.

As best illustrated in FIG. 3, the headband 12 includes a browband 23 which is intended for disposition in contact with the forehead 19, and an attachment strap 25 which is intended for contact with the hair 21 of the user 18. Together the browband 23 and attachment strap 25 form the headband 12 which extends circumferentially around the head 16 of the user 18. In a preferred embodiment, the browband 23 is formed from two separate enclosures referred to herein as an upper tube 30 and a lower tube 32.

Each of these tubes 30, 32 has an associated axis 34, 36 which extends from a center line 38 circumferentially right and left to a first end 41 and a second end 43 of the browband 23. The browband 23 is further characterized by a top surface 45 associated with the upper tube 30 and a bottom surface 47 associated with the lower tube 32. A common stitch 50 separates the tubes 30, 32 so that they have a tangential relationship in cross section with their respective axes 34, 36 extending generally parallel around the browband 23.

In a preferred embodiment, the tubes 30, 32 have a radial cross section which is greater near the center line 38 and tapers toward the ends 41 and 43. Generally, in such an embodiment at least one of the first tube 30 and the second tube 32 has in radial cross section a diameter which decreases with progressive positions from the centerline 38 circumferentially to the first end 41, and with progressive positions from the center line 38 circumferentially to the second end 43. Although the axis 34, 36 of the tubes 30, 32 are generally parallel in such an embodiment, they tend to converge slightly along the tapers.

Of particular interest to the present invention is the cooling material 52 which is preferably enclosed in the tubes 30 and 32. In a preferred embodiment, this cooling material 52 has a crystalline structure and is formed from a hydroscopic and hydrophilic compound such as a polymer in the form of a crosslinked modified polyacrylate. This polymer is non-reactive and therefore 100% non-toxic. The crystals, designated by the reference numeral 54, are illustrated in a wet, swollen state in FIG. 4, and in a dry, contracted state in FIG. 5.

Figure 4:
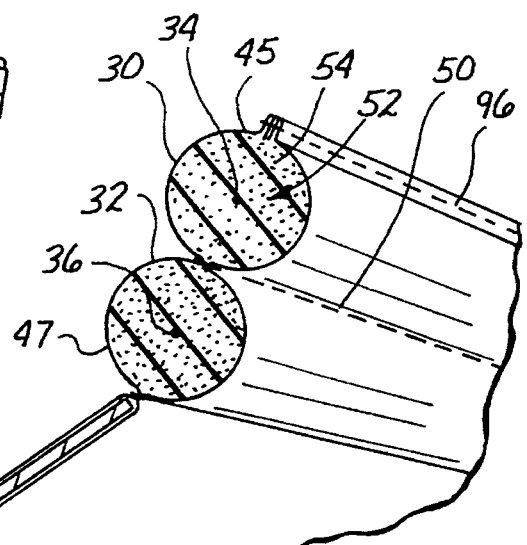
FIG. 4 is a cross section view taken along lines 4—4 of FIG. 2.
Figure 5:
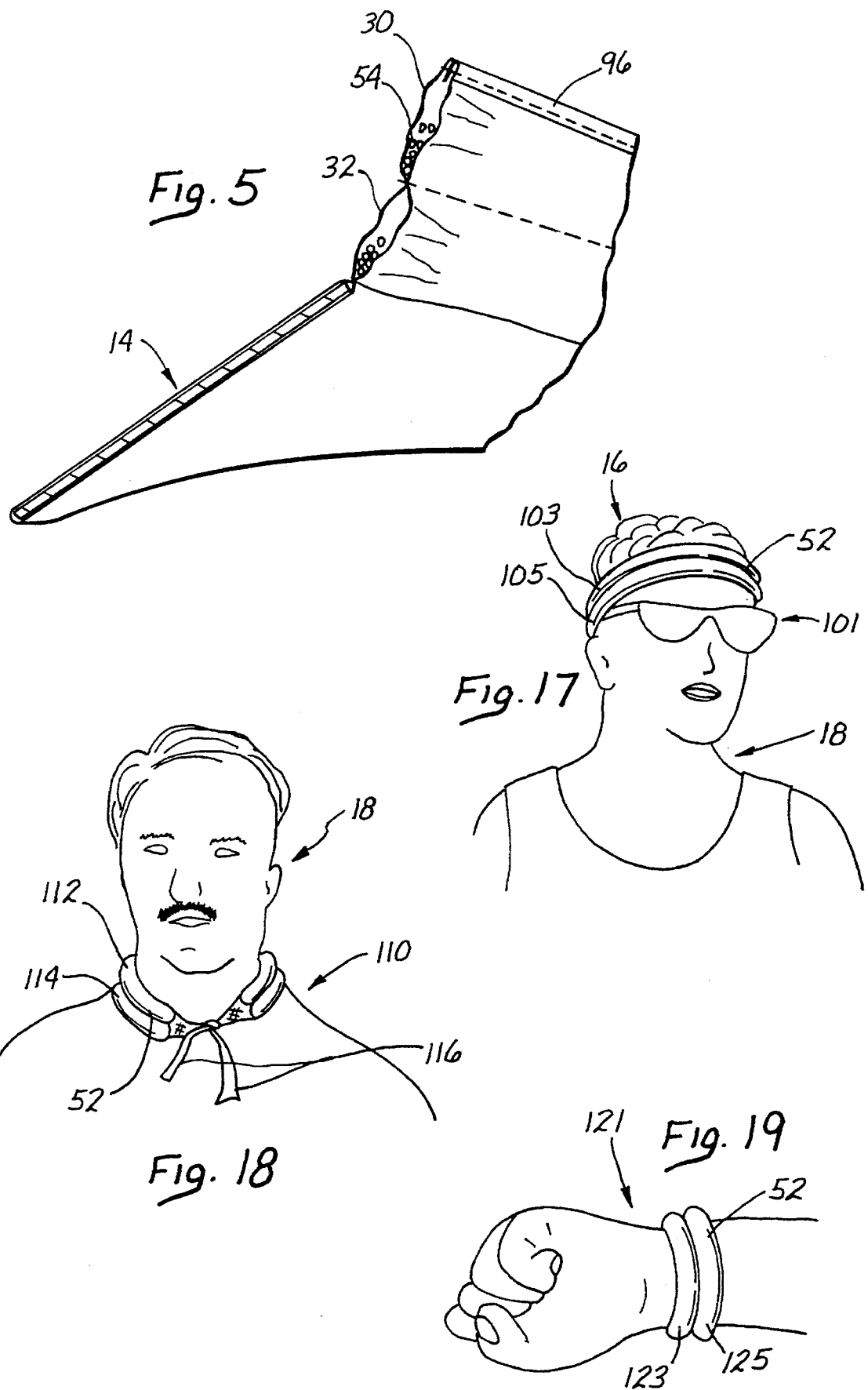
FIG. 5 is a cross section view similar to FIG. 4 and illustrating the cooling material in a non-absorbent state.

The material forming the tubes 30, 32 is preferably permeable by water but impermeable to the crystals 54 in either the dry state illustrated in FIG. 5 or the swollen state illustrated in FIG. 4. These characteristics permit the visor 10 to be soaked in water thereby permitting the crystals 54 to absorb water and swell from the dry state to the swollen state. The preferred crystals formed from crosslinked polyacrylate will absorb water in a magnitude sufficient to increase their weight and expand their volume by a factor of more than 100. It is the evaporation of this water from the crystals 54 which produces the highly desirable cooling effect associated with the visor 10.

The eyeshade 14 extends downwardly and outwardly from the bottom surface 47 of the tube 32. A fixed relationship between the browband 23 and eyeshade 14 is enhanced by attaching the eyeshade 14 to the tube 32 along a substantial length of the surface 47. The eyeshade 14 is typically formed from a water tolerant insert 56 which in a preferred embodiment is formed from polypropylene or some other plastic material.

Figure 6:
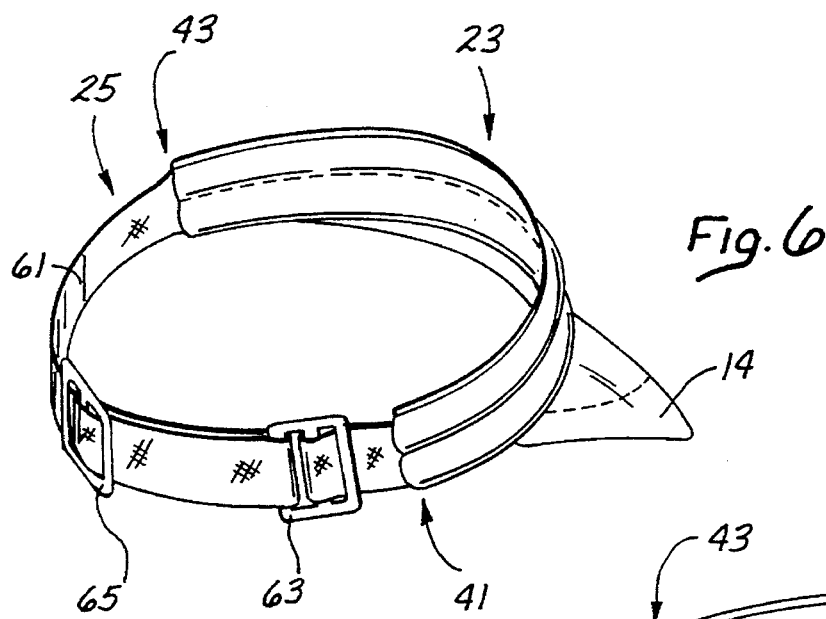
FIG. 6 is a side perspective view illustrating a headband including a browband and buckle attachment strap in one embodiment of the visor.
Figure 7:
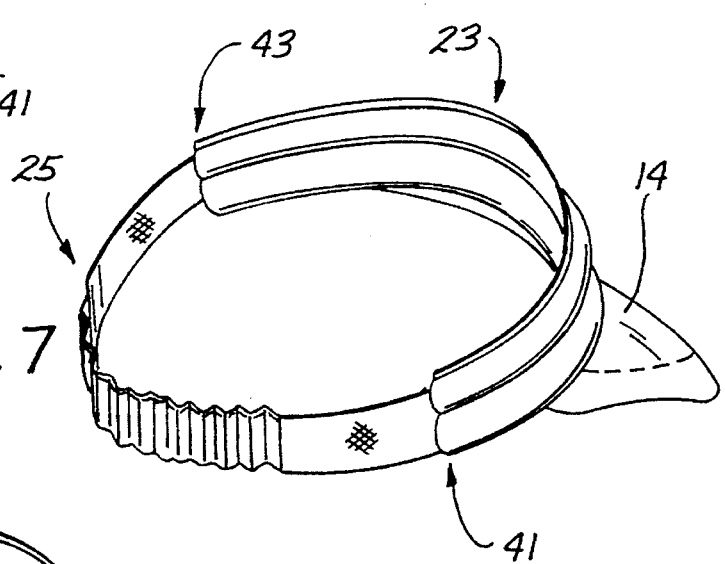
FIG. 7 is a side perspective view similar to FIG. 5 and illustrating an elastic attachment strap in an additional embodiment of the invention.
Figure 8:
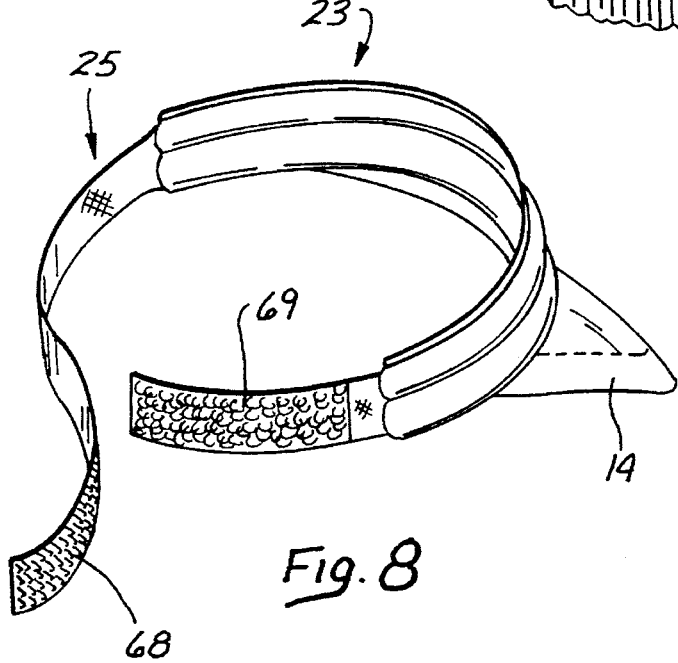
FIG. 8 is a side perspective view similar to FIG. 5 with a hook and loop attachment strap.

The attachment strap 25 is connected between the ends 41 and 43 of the browband 23 thereby forming the headband 12. Various embodiments of the attachment strap 25 are illustrated in FIGS. 6 to 8. For example, in FIG. 6, the attachment strap 25 is formed from two separate straps 58, 61 each terminating at a buckle 63, 65, respectively. The strap 61 extends from the second end 43 through the buckle 65 and the buckle 63 where it is bent back on itself to terminate at the buckle 65. The position of the buckle 65 along the strap 61 is adjustable to vary the length of the strap 61. Accordingly, the attachment strap 25 has a length which is variable between the ends 41 and 43 of the browband 23. This provides the overall headband 12 with a variable circumference adapted to fit the head 16 of any user 18.

The attachment strap 25 of FIG. 7 includes an elastic band 67 which is also variable in length between the ends 41 and 43 of the browband 23. The elastic band 36 is adjustable between an expanded position and a contracted position, and is biased to the contracted position.

FIG. 8 illustrates a further embodiment of the attachment strap 25. In this case, the two straps 58 and 61 are provided with a pair of opposing patches 68 and 69 of hook and loop material. These patches 68, 69 can be joined at a variety of positions each associated with a different length of the attachment strap 25.

The process for manufacturing the visor 10 is illustrated in FIGS. 9 through 13. Initially, the eyeshade 14 is formed as a subassembly including two pieces 70, 72 of crescent-shaped fabric. Each of the pieces 70, 72 has an associated convex edge 74, 76 and an associated concave edge 78, 81. A seam 83 is formed along the convex edges 74, 76. The resulting structure is inverted along the seam 83 so that the convex edges 74, 76 are disposed within a crescent-shaped cavity 85. The crescent-shaped insert 56 is disposed in this cavity 85 and the concave edges 78–81 are joined along a seam 87. This completes the subassembly of the eyeshade 14 as best illustrated in FIG. 10.

The browband 23 is formed from two pieces 90, 92 of the permeable fabric. These pieces of fabric 90, 92 can be laid alongside the subassembly of the eyeshade 14 and joined to the eyeshade 14 along a stitch 94. This enables the pieces of fabric 90, 92 to be bent back on themselves and away from the eyeshade 14 as illustrated in FIG. 12.

In a preferred embodiment, the stitch 94 is more closely spaced to the insert 56 than the seam 87. With this construction, the stitch 94, which joins the eyeshade 14 and the browband 23, is hidden and any outside view of the visor 10.

The common seam 50 can then be formed between the pieces of fabric 90, 92 along with a seam 96 which is formed along the top surface 45 of the browband 23. This construction forms the two tubes 30, 32 which are open at the ends 41, 43.

After the tubes 30, 32 are formed, the crystals 54 or other cooling material 52 can be introduced into the tubes 30, 32. Opposing ends of the attachment strap 25 can be sewn or otherwise attached to the ends 41, 43 of the browband 23. This not only seals the tubes 30, 32 with the crystals 54 inside, but also completes formation of the adjustable headband 12.

Figure 13:
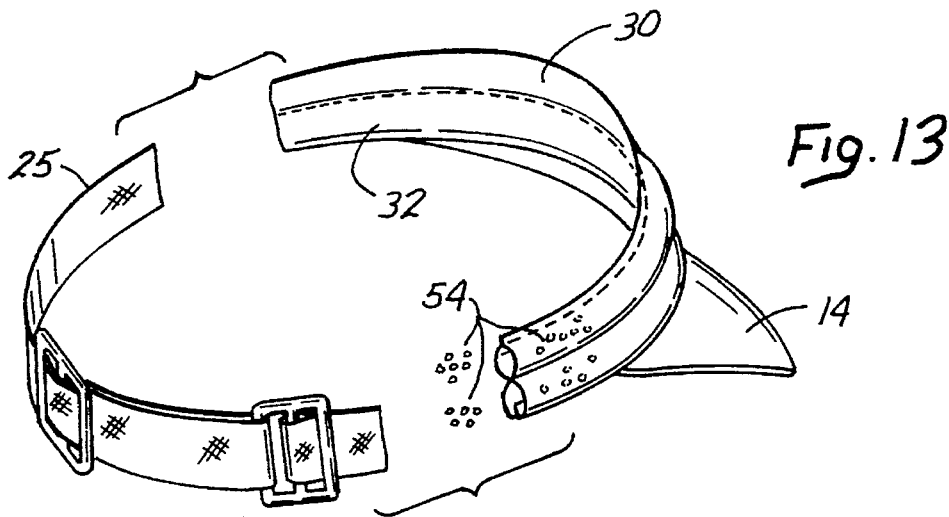
FIG. 13 is a top perspective view of the visor illustrating the steps of inserting a cooling material into the tubes of the browband and attaching the adjustment strap to complete the headband of the visor.
Figure 14:
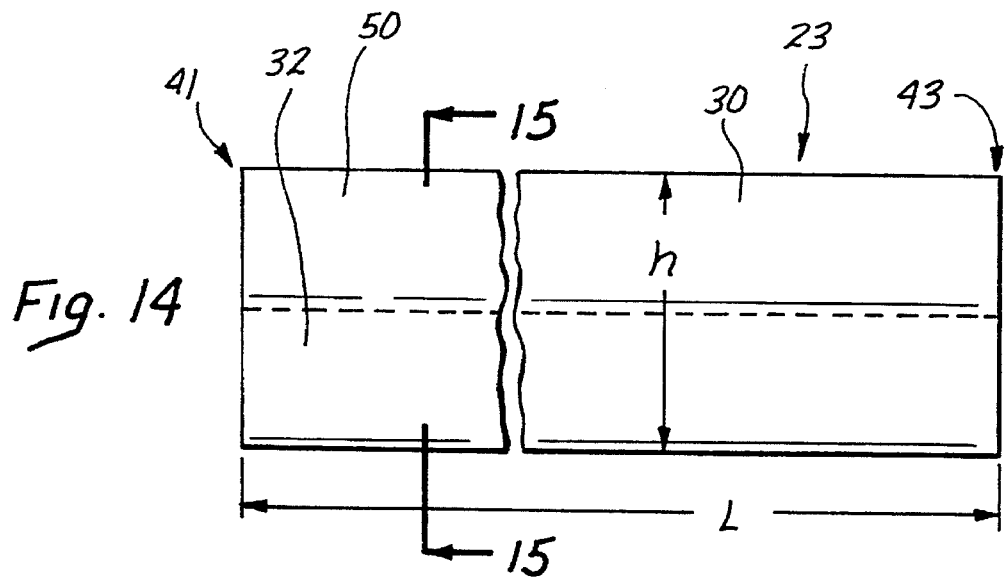
FIG. 14 is a schematic front elevation view of the browband in a generally planar configuration.

Of particular interest in the present invention is the need to balance the requirements relating to the cooling area of contact and the bulk or volume of the swollen cooling material 52. For simplicity of explanation, the browband 23 is illustrated in FIG. 14 in a flattened rather than rounded configuration. Thus, the browband in FIG. 13 is disposed generally in the plane of the page extending from the first end 41 to the second end 43. The height of the browband is shown by the letter "h" while the length of the browband is shown by the letter "L". From this view it is apparent that the area of contact between the browband 23 and the forehead 19 of the user 18, is the product of "L" and "h". If "h" and "L" are held constant, but the number of tubes, such as the tubes 30, 32, are varied, the ratio of area of contact (A) to volume of cooling material (v) varies considerably. Derivation of this ratio is set forth below in Formula I:

$$\text{Ratio} = \frac{A}{V} = \frac{hL}{X\pi r^2 L} = \frac{4X}{\pi h} \quad \text{(Formula I)}$$

where r=h/2X=the radius of the tubes;

h=the height of the browband 23;

L=the length of the browband 23; and

X=the number of tubes.

In the interest of maximizing the area of contact while minimizing the bulk, weight and volume of the cooling material 52, it is desirable to increase this ratio as much as possible. From Formula I it can be seen that adding one additional tube to the browband 23 while maintaining the height "h", will increase this ratio by a factor of 4.

Figure 15:
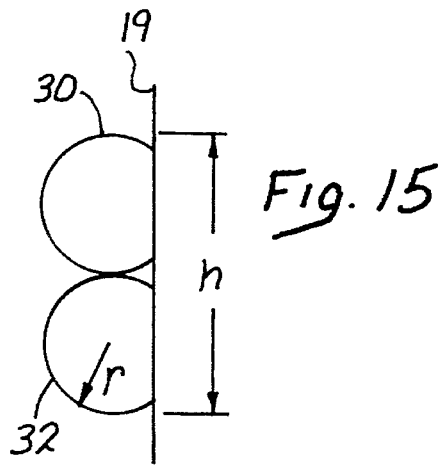
FIG. 15 is a cross section view taken along lines 15—15 of FIG. 14 in a two-tube embodiment of the browband.
Figure 16:
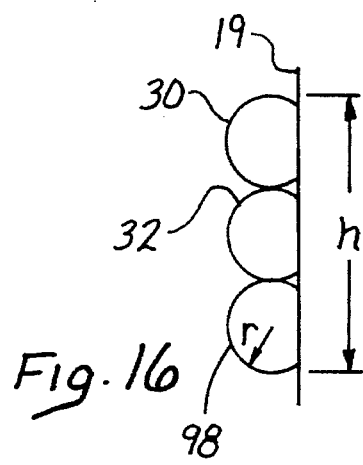
FIG. 16 is a cross section view similar to FIG. 15 of a three-tube embodiment of the browband.

While a relatively high ratio may be desirable to increase the area of contact and decrease the volume, it is also desirable to supply the material 52 in a quantity which will provide for cooling over an extended period of time. There are many environmental factors, such as temperature and humidity, which affect the length of time over which the absorbed water evaporate from the cooling material 52. However, it is generally felt that an evaporation period of five to ten hours is preferred. In an embodiment wherein the length of the browband 23 is about eleven inches and the height of the browband 23 is about 1.5 inches, a single tube embodiment will contain about 21 cubic inches of the cooling material 52. By comparison, a two-tube embodiment, such as that illustrated in FIG. 15, includes only 10.6 cubic inches. As additional tubes are added, the volume of cooling material 52 drops to about 7 cubic inches in a three-tube embodiment (FIG. 16) and only about 5 cubic inches in a four-tube embodiment (not shown). Of course, these volumes are theoretical and will vary with the specific shape of the tubes, such as the tubes 30 and 32. If the tubes 30, 32 are tapered or otherwise reduced in cross sectional area, the volume will drop accordingly.

With respect to the duration of the cooling period, it has been found that between 6 and 15 cubic inches of material is required for an acceptable duration of the cooling period. In accordance with the foregoing analysis, this would indicated that either the two-tube or three-tube embodiments would be preferred. As previously noted with reference to Formula I, the three-tube embodiment provides the higher ratio between area and volume. However, the extended period of cooling provided by the two-tube embodiment makes this the most preferred form of the invention.

Although this concept has been disclosed with reference to the visor 10, it will be apparent that the invention can be embodied in other forms of cooling apparel. For example, the concept of a multiple tube headband can be embodied without an eyeshade, such as the eyeshade 14, as illustrated in FIG. 17. This headband 101 could be formed of multiple tubes 103 and 105 which extend around substantially the entire circumference of the user's head 16. The increased volume provided by this extended tube configuration would contain a larger volume of the crystals so that the ratio of Formula I might encourage one to form the headband 101 from three or four tubes.

A neckband 110 including multiple tubes such as the tubes 112 and 114 as illustrated in FIG. 18. In this embodiment, the neckband 112 can be secured with end ties 116. Since the neck of the person 18 generally has a smaller circumference than the head 16, the neck band 110 might benefit from the larger volume associated with the two-tube embodiment.

FIG. 19 illustrates a wristband 121 including tubes 123 and 125. In this case, the much smaller circumference associated with the wrist of the user might favor a single tube embodiment which would provide the largest volume of the cooling material 52.

Although the disclosure has been generally limited to a cooling material 52 which is liquid absorbent to promote evaporation, it will be apparent that other types of cooling materials can be used to form cooling apparel. Where liquid absorbent materials are used, liquids other than water may be desirable for certain applications.

With the wide variations possible with the materials, fabrics and constructions of various items of apparel, which are all within the scope of this concept, one is cautioned not to restrict the invention to the embodiments which have been specifically disclosed and illustrated, but rather encouraged to determine the scope of the invention only with reference to the following claims.

I claim:

1. A visor adapted to be worn on the head of a user, the visor comprising:

a browband having a top surface and a bottom surface each extending between a first end and a second end of the browband;

attachment means extending between the first end and the second end of the browband and forming with the browband a headband, the attachment means having a variable length to facilitate snug engagement of the headband with the head of the user;

a sunshade extending outwardly from the bottom surface of the browband in a fixed relationship with the browband;

a first tube included in the browband and having a first axis, the first tube defining the top surface between the first end and the second end of the browband;

a second tube included in the browband and having a second axis, the second tube defining the bottom surface between the first end and the second end of the browband;

the first tube being disposed tangentially to the second tube with the first axis generally parallel to the second axis; and a cooling material disposed in at least one of the first tube and the second tube.

2. The visor recited in claim 1 wherein the browband includes a center line disposed generally equidistant between the first end and the second end, and the sunshade further comprises:

at least one of the first tube and the second tube having in radial cross section a diameter which decreases with progressive positions from the center line circumferentially to the first end of the browband, and from the center line circumferentially to the second end of the browband.

3. The visor recited in claim 1 wherein the attachment means includes an elastic band adjustable between an expanded position and a contracted position, the elastic band being biased to the contracted position.

4. The visor recited in claim 2 wherein the cooling material is absorbent of an evaporative liquid.

5. The visor recited in claim 4 wherein the evaporative liquid is water.

6. The visor recited in claim 5 wherein the water absorbent material is a crosslinked polymer.

7. The visor recited in claim 1 wherein:

the number of tubes including the first tube and the second tube is "X";

each of the tubes has a radius "r" and a length "L";

the browband has a height "h";

the interior volume of the tubes is equal to about $X\pi r^2 h$;

the area of contact between the browband and the head of the user is about "hL"; and the ratio of the area of contact between the browband and the head of the user to the interior volume of the tubes is not less than about $8/\pi h$.

8. The visor recited in claim 7 wherein the interior volume of the tubes is between about 6 and 16 cubic inches.

9. The visor recited in claim 1 further comprising a stitch joining the sunshade to the second tube, the stitch being hidden in an outside view of the visor.

10. The visor recited in claim 6 wherein the polymer is a crosslinked polyacrylate.

11. A cooling band system adapted to be worn in contact with the body of a user, comprising:

a cooling strip extending between a first end and a second end;

attachment apparatus extending between the first end and the second end of the cooling strip and forming with the cooling strip a band, the attachment apparatus having a variable length to facilitate snug engagement of the body of the user;

a first tube included in the cooling strip and having a first axis, the first tube extending between the first end and the second end of the cooling strip;

a second tube included in the cooling strip and having a second axis, the second tube extending between the first end and the second end of the cooling strip;

the first tube being disposed tangentially to the second tube with the first axis of the first tube being generally parallel to the second axis of the second tube; and a cooling material disposed in at least one of the first tube and the second tube.

12. The cooling band system recited in claim 11 wherein the system forms a visor further comprising:

a sun shade extending outwardly from the band in generally fixed relationship with the cooling strip.

13. The cooling band system recited in claim 11 wherein the system forms a headband.

14. The cooling band system recited in claim 11 wherein the system is adapted to be worn as a neckband.

15. The cooling band system recited in claim 11 wherein the system is adapted to be worn as a wristband.

* * * * *